United States Patent [19]

Mahmud

[11] 4,212,306

[45] Jul. 15, 1980

[54] BREAST EXAMINATION DEVICE AND METHOD

[76] Inventor: Khalid Mahmud, 6601 Southcrest Dr., Minneapolis, Minn. 55435

[21] Appl. No.: 907,001

[22] Filed: May 18, 1978

[51] Int. Cl.² .................... A61B 6/08; G01N 33/16
[52] U.S. Cl. ................................................. 128/665
[58] Field of Search ............. 128/2 A, 2 R; 33/664, 33/665

[56] References Cited

U.S. PATENT DOCUMENTS

| | | | |
|---|---|---|---|
| 3,556,081 | 1/1971 | Jones | 128/2 A |
| 3,578,971 | 5/1971 | Lasky | 250/50 |
| 3,648,685 | 3/1972 | Hepp et al. | 128/2 R |
| 3,971,950 | 7/1976 | Evans et al. | 250/456 |

OTHER PUBLICATIONS

Cover, Table of Contents, and pp. 8 and 13 of *Medical World News,* Jan. 1978, McGraw Hill, Inc.

*Primary Examiner*—Willis Little
*Attorney, Agent, or Firm*—James R. Haller

[57] ABSTRACT

A method and apparatus for breast examination. A pair of spaced, transparent plates are provided between which a female breast may be gently compressed and flattened. A beam of light from a movable light source is directed through the plates and flattened breast, and the light source may be moved to sequentially illuminate substantially the entire breast between the plates. The beam of light may be view through the plates and breast to permit visual detection of areas of breast tissue having lesser transparency and which may be suggestive of tumor growth.

16 Claims, 6 Drawing Figures

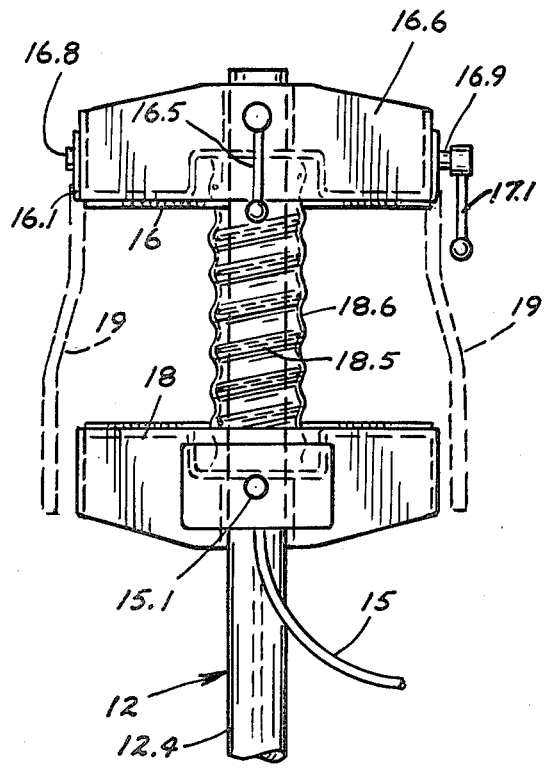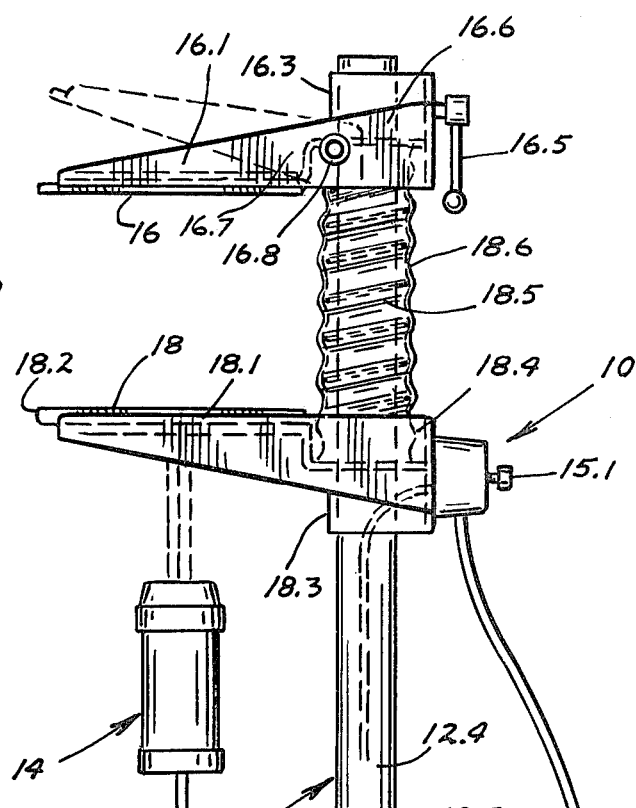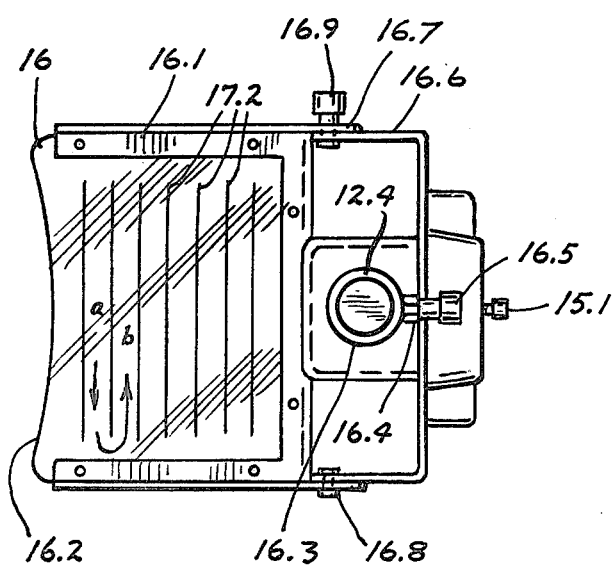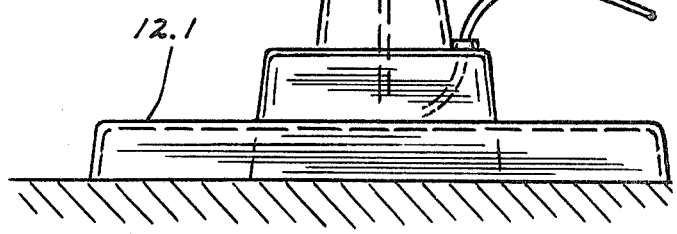

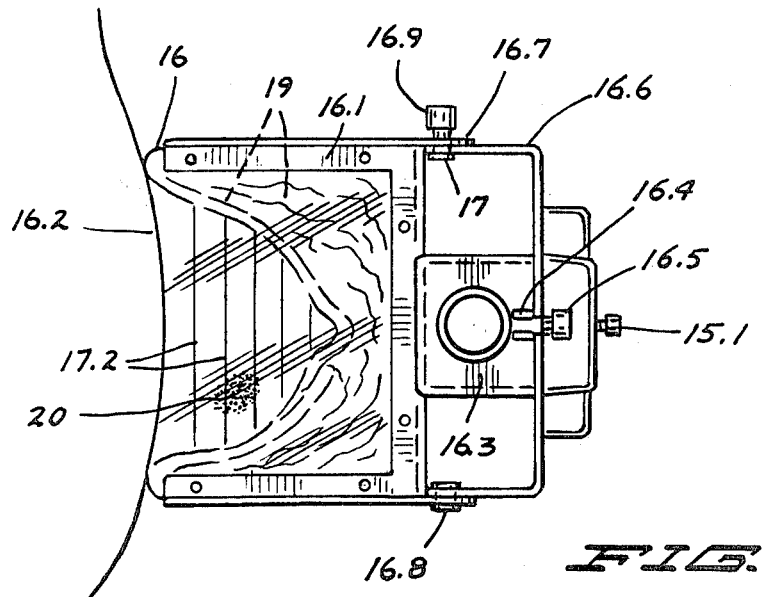
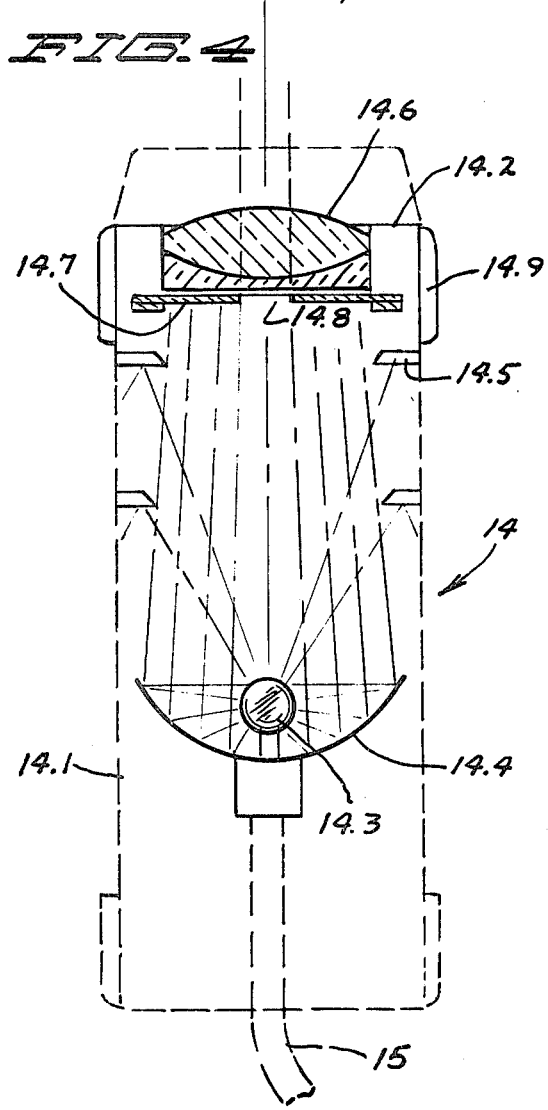
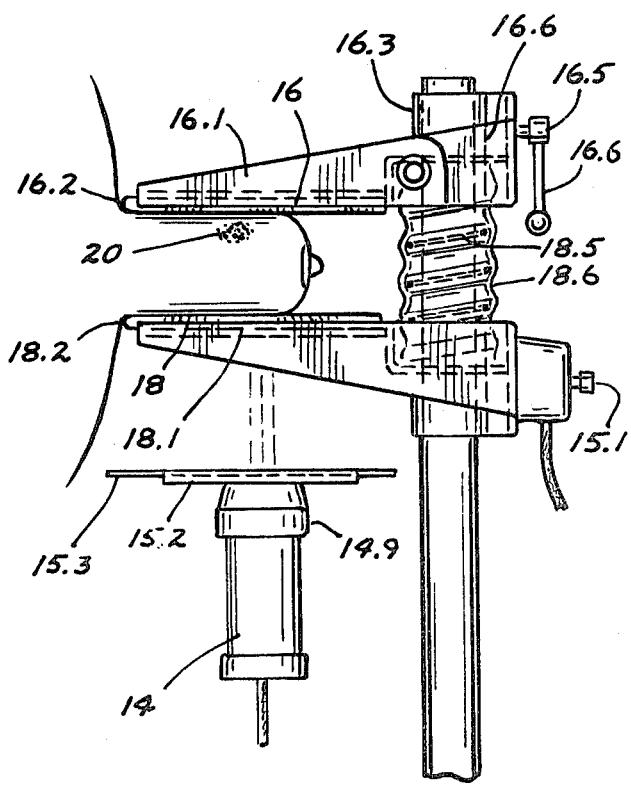

BREAST EXAMINATION DEVICE AND METHOD

BACKGROUND OF THE INVENTION

The success of medical treatments for breast cancer in human females is highly dependent upon the early detection of cancerous growths or pre-malignant tumors. The most common methods of detection involve palpation of breast tissue and mammography. Tumor detection by palpation, although desirable, is far from satisfactory, particularly in small, early stage tumors. Mammography provides perhaps the most reliable method of detection. Exposure of the breasts to x-rays in this procedure, however, may not be safe if used repeatedly as a routine screening procedure.

A method of visual breast examination which could be used in conjunction with palpation techniques and which could avoid the possible dangers associated with repeated, routine mammography is much to be desired.

SUMMARY OF THE INVENTION

The present invention provides a method and apparatus for detecting tumorous growths in the female breast, and for distinguishing cysts from solid tumors. The method involves gently compressing and flattening the breast between a pair of plates transparent to visible light, and then passing a beam of light of substantially uniform cross-section in a direction normal to and through the plates and breast tissue between the plates. The light source is viewed by the physician through the plates and breast tissue to detect areas of the breast tissue of lesser transparency, which may be suggestive of tumor growth. To enhance delineation and definition of such areas, the beam thickness and intensity may be varied as desired. Desirably, the light source is moveable so that substantially all portions of the breast tissue between the plates is examined, and it is preferable that the light source be moved in a predetermined pattern to ensure sequential illumination of substantially all portions of the breast tissue. Movement of the light source, as described, tends to move specifically define the shape and location of tumorous masses. The beam of light may be monochromatic or polychromatic, as desired, and all portions of the visible spectrum, including the near ultraviolet and near infrared, can be used as desired to obtain optimum results.

The instant invention also provides an apparatus comprising a pair of spaced plates transparent to visible light. Means are provided to support the plates relative to each other and to permit the plates to be moved toward and away from one another to enable the breast to be captured and gently compressed and flattened between the plates. The apparatus includes means defining a source of visible light positionable exteriorly of the plates for producing a light beam which is directable through the plates and flattened breast tissue. The light source means includes means permitting the diameter or the intensity or both of the light beam to be varied as desired, and may include means for varying the wavelength of the beam. The apparatus further desirably includes screening means incorporating opaque material for screening the examiner's eyes from the light beam at edges of the flattened breast section.

BRIEF DESCRIPTION OF THE DRAWING

FIG. 1 is a side view of an apparatus of the invention, shown partly broken-away;

FIG. 2 is a broken-away view taken from the right side of FIG. 1;

FIG. 3 is a top view of the device of FIG. 1;

FIG. 4 is a partially broken-away, cross-sectional view in schematic form of the light source shown also in FIG. 1;

FIG. 5 is a top view of the device showing the position of a breast held therewithin; and FIG. 6 is a side view of the device shown in FIG. 5.

DESCRIPTION OF THE PREFERRED EMBODIMENT

With reference to FIGS. 1-3, a representative apparatus of the invention is designated generally as 10 and includes frame means designated generally as 12, a light source designated generally as 14, and a pair of plates, designated generally as 16, 18. As shown, the plates are mounted to the frame, and the light source 14 may conveniently be connected to or carried by the frame as well.

The frame 12 includes a heavy base member 12.1 for supporting the apparatus on a floor. A pedestal 12.2 arises from the base member and includes a lower, hollow portion 12.3 and an upper portion 12.4 telescopically received in the lower portion so that the upper portion can be raised and lowered as desired. Means are provided to releasably lock the upper and lower pedestal portions together, such means including, for example, a set screw 12.5 threaded into the lower pedestal portion and engageable with the upper pedestal portion, the set screw being tightened or loosened by movement of a handle 12.6 to which the set screw is attached, all in a manner known to the art.

The plates 16, 18 are of a transparent material such as glass. The upper plate 16 is carried by a frame 16.1 which borders the plate on three sides. The plate is generally rectangular but is provided with a slightly concavely-shaped free front edge 16.2, the curvature of the latter edge being such as to fit closely against the human chest wall in the vicinity of the breast. The edge 16.2 is smoothly rounded to avoid tissue irritation, and may, if desired, be provided with a lining of sponge rubber or fabric or other soft material.

A bearing ring 16.3 slideably receives the upper edge of the pedestal upper portion 12.4, as shown perhaps best in FIG. 3. The bearing is held to the pedestal by means of a set screw 16.4 operated by a handle 16.5, thus permitting the bearing to be vertically positioned upon, and locked to, the upper portion of the pedestal. Rigidly attached to the bearing is a generally U-shaped 16.6, the legs of which extend generally forwardly for pivotal connection to rearwardly extending arms 16.7 of the frame 16.1. The pivotal connection employs pivot pins 16.8, 16.9 of which the latter is provided with a threaded coupling 17 threadably engaging the pin 16.9 to permit the frames 16.1, 16.6 to be locked together. The pin 16.9 is provided with an exterior handle 17.1 for manual operation.

The lower plate 18 is similarly provided with a slender, peripheral frame 18.1 about three sides of its periphery with the free front edge 18.2 of the plate being gently rounded and slightly concave in the same manner as the plate 16. The lower plate is provided with a bearing 18.3 which is locked to the upper portion of the pedestal, the bearing including a frame 18.4 supporting the frame 18.1. The plate 18 shown in the drawing is hence rigidly fixed to the pedestal, although it may be desirable to permit the plate 18 to move upwardly or downwardly upon the pedestal or to tilt in the same manner as described above with reference to plate 16.

A helical spring 18.5, received about the circumference of the upper portion of the pedestal, is held in gentle compression between the bearings 16.3, 18.3 to gently urge the plates apart. The spring 18.5 may be covered with a flexible, plastic sleeve 18.6. Other means of gently urging the plates apart, of course, may be employed as well.

The source of visible light, shown generally as 14 in the drawing, is provided with a configuration enabling it to be easily held in the hand and moved back and forth beneath the lower plate 18, the beam of light emitted from the source passing upwardly through both plates. As shown best in FIG. 4, the light source 14 may have an exterior, cylindrical barrel 14.1 which is closed at its lower end and which has an open upper end 14.2. Within the barrel is positioned a light source, such as an electric light bulb 14.3. A parabolic reflector 14.4 is positioned beneath the light source to reflect light rays emitted by the source 14.3 in a generally upward direction. The inner surface of the barrel 14.1 desirably is of non-reflective, blackened material, and the barrel is provided with one or more sets of light-absorbing annular rings 14.5 to eliminate spurious light rays. At its upper end, the barrel may be provided with a compound lens 14.6 to render generally parallel the light rays emitted from the barrel. An adjustable plate or series of plates 14.7 are positioned immediately below the lens 14.6 and provide a central aperture 14.8 through which the light rays pass, the aperture thus controlling the cross-sectional area (e.g., the diameter of a circular beam) of the collimated light issuing from the barrel. The plate or plates 14.7 defining the aperture desirably are of the iris type employed in cameras, and the aperture may be varied by turning a manually operable ring 14.9 at the forward end of the barrel. In another embodiment, the plate 14.7 may be replaced with one or more other plates having apertures of varying sizes to permit varying of the light beam diameter. Variable apertures are well-known to the art, and need not be described further. The light source 14.3 desirably is electrically powered, and an electric power cord 15 extends through the bottom end of the barrel to the frame 18.4 of the lower plate 18, and thence downwardly through the interior of the pedestal, the cord exiting at the pedestal base 12.1 so that the cord can be plugged into an ordinary electrical outlet. The frame 18.4 may be provided with an external switch, shown as 15.1 in FIG. 1, to enable the light source to be switched on and off as desired. The switch 15.1 may include a rheostat for varying the intensity of the light beam, or a rheostat and switch may be incorporated in the barrel 14.1.

The beam, as mentioned, may be of light having a wavelength or a range of wavelengths falling within the visible spectrum (including near ultraviolet and infrared regions). As shown in FIG. 6, the light source may be provided with an elongated, exterior frame 15.2 bearing a strip 15.3 of colored film having sequential portions transparent to different regions of the visible spectrum, the strip being slidable in the frame to place the desired portion of the film in alignment with the light beam to filter the beam. The film may be provided in disc form, with the light source having means permitting the disc to pivot about its center so that a desired portion of the disc may filter the light beam. Desirably, the portions of the strip or disc transparent to different wavelengths of light merge into one another so that movement of the strip or disc results in a continuous gradual variance in the wavelength of transmitted light. The thus described filter means may, of course, be otherwise placed anywhere between the light source and bottom plate in position to intercept the light beam.

The plates 16, 18 desirably are of clear, uncolored glass and in any event are transparent to visible light. The plates may be tinted, however, if desired, to improve the view afforded the physician therethrough. The plates 16, 18 may, of course, be of other transparent material such as plastic. The upper plate 16 is desirably provided with a series of scribed, parallel, spaced lines 17.2, the lines providing a visual "track". In operation, the light beam may be passed horizontally in one direction beneath the lower plate so that the beam of light is viewed as moving between two of the scribed lines, as shown by path "a" in FIG. 3. When the edge of the plate has been reached, the light source is advanced to the adjacent pair of scribed lines and is then moved so that it is viewed between these lines, as shown by arrow "b" in FIG. 3. The movement of the light source along a predetermined path in this manner insures that all portions of the breast will be viewed by the physician.

As previously mentioned, the diameter of the light beam emitted by the barrel may be varied as desired. For example, the physician may begin examination by employing a light beam of rather large diameter, e.g., 1-2 cm., to see if dark patches or visual discontinuities are immediately visible in the breast tissue. Thereafter, the diameter of the beam may be narrowed for more precise examination. When an irregular mass (designated 20 in FIGS. 5 and 6) is discovered, the diameter of the light beam may be varied as desired to permit the physician to not only more readily view the mass, but also to obtain an indication of the size and precise location thereof. Although impingement of the light source upon breast tissue will cause the breast tissue as a whole to be illuminated slightly, the light source can nonetheless be viewed through the plates and breast tissue as a circular beam which can be partially or substantially wholly obstructed by an irregular tissue mass.

The pedestal 12.2 is desirably of sufficient height so as to position the plates 16, 18 at generally chest level for adult, female patients in a sitting position, but the plates as a whole can be moved up and down by varying the height of the upper pedestal portion 12.4 as described above. With the plates 16, 18 in their widely separated position as shown in FIG. 1, the breast of a patient is positioned upon the lower plate 18 with the forward edge 18.2 of the plate pressing gently against the chest wall of the patient below the breast. The upper plate is then brought downward gently against pressure of the spring 18.5 causing the breast to be compressed and flattened slightly between the plates, the forward edge 16.2 of the upper plate similarly bearing gently against the chest wall of the patient above the breast. When the appropriate flattening or compression of the breast has been obtained, the handle 16.5 is operated to lock the upper plate in position with respect to the lower plate. Desirably, the plates 16, 18 are maintained parallel to one another so that the section of breast captured therebetween is of a uniform thickness. It may be desirable, of course, in some cases to permit the upper plate to tilt upwardly slightly as shown in phantom lines in FIG. 1 to accommodate breasts of different sizes.

After the breast has been captured between the plates 16, 18, as shown in FIG. 6, an opaque material is applied to the exposed sides of the breast to prevent light from escaping outwardly. The opaque material may be substantially any opaque material which can be configured closely to the edges of the breast without discomfort to the patient. For example, the opaque material may be of a soft clay or dough. In one embodiment (FIGS. 2 and 5), the opaque material may take the form of an opaque fabric or film, such as black velvet, sheets 19 of the material being loosely attached to side edges of the top frame 16.1, as shown in phantom lines in FIG. 2. The material is then gently stuffed between the plates and into contact with exposed edges of the breast so as to substantially block the passage of the light beam through the plates about the edges of the breast. The actual examination will take place in a darkened room and the opaque material effectively prevents the light beam from inadvertently striking the examining physician's eyes and reducing visual acuity accordingly. Further screening means, in addition to the opaque material, may be employed to guard the physician's eyes; e.g., a sheet of opaque material such as cardboard may extend laterally outwardly from the lower plate or frame. The opaque material may take the form of, or include, a flexible sheet of bendable, yieldable material such as lead, which, when molded to the contours of the breast edges, retains its molded shape until the examination has been completed.

The examination room is darkened, the light source 14 is turned on and the ring 14.9 is turned to provide a fairly large diameter light beam extending upwardly from below the lower plate 18 so that the light beam can be viewed by the physician looking downwardly through the top plate 16. The light source 14, being held by the physician, is then passed back and forth as described above. Upon discernment of a tumorous mass or the like within the breast, the physician may narrow or enlarge the diameter of the light beam, or vary its wavelength or intensity, so as to more clearly visualize the mass and to determine its location and size.

Thus, manifestly there has been provided a method and apparatus for harmlessly detecting the presence of tumorous masses in breast tissue. The method and apparatus does not make use of possibly harmful x-rays, and the apparatus is entirely in the control of the physician during examination. Furthermore, the examination procedure is not harmful to the patient, and little if any pain is experienced. The apparatus and method can be employed easily and quickly in non-hospital environments such as doctor's clinics and the like, and are particularly adapted for use in routine physical examinations. The apparatus is comparatively small and occupies little storage space and does not make use of expensive x-ray machines or viewing screens.

While a preferred embodiment of the present invention has been described, it should be understood that various changes, adaptations, and modifications may be made therein without departing from the spirit of the invention and the scope of the appended claims.

What is claimed is:

1. Apparatus for the examination of the female breast for tumors or the like, comprising a pair of spaced plates transparent to visible light;
   means for supporting the plates relative to each other and permitting the plates to be moved toward and away from one another to enable the breast to be captured and gently compressed and flattened between the plates; and
   a source of visible light positionable exteriorly of the plates for producing a narrow beam of light directable through the plates and flattened breast, said source being movable with respect to the plates generally normal to the direction of said beam to enable sequential illumination of substantially the entire breast captured between the plates.

2. The apparatus of claim 1 wherein said light source includes means for varying the diameter of the narrow beam of light.

3. The apparatus of claim 1 including means for varying the wavelength of the light beam.

4. The apparatus of claim 1 wherein the visible light is substantially monochromatic.

5. The apparatus of claim 1 wherein said means for supporting the plates relative to each other includes means maintaining confronting surfaces of the plates parallel.

6. The apparatus of claim 5 including means gently urging the plates apart.

7. Apparatus for the examination of the female breast for tumors or the like, comprising a pair of spaced plates transparent to visible light, means for supporting the plates relative to each other and permitting the plates to be moved toward and away from one another to enable the breast to be captured and gently compressed and flattened between the plates, and a source of visible light positionable exteriorly of the plates for producing a narrow beam of light directable through the plates and flattened breast, said source being movable with respect to the plates generally normal to the direction of the beam to enable illumination of substantially the entire breast between the plates, at least one of said plates including visible, spaced, parallel scribe lines thereacross, the spacing between adjacent lines being substantially the same as the diameter of the light beam.

8. The apparatus of claim 7 including means for varying the diameter of the light beam.

9. Apparatus for the examination of the female breast for tumors or the like, comprising a pair of spaced plates transparent to visible light, means for supporting the plates relative to each other and permitting the plates to be moved toward and away from one another to enable the breast to be captured and gently compressed and flattened between the plates, a source of visible light positionable exteriorly of the plates for producing a narrow beam of light directable through the plates and flattened breast, and screening means positionable to screen the examiner's eyes from the light beam at edges of the flattened breast.

10. The apparatus of claim 1 wherein the light source includes a manually supportable barrel open at its upper end, a source of light within the barrel, and means carried by the barrel for varying the cross-sectional area of the light beam emitted by the light source.

11. The apparatus of claim 10 including means for varying the wavelength of the emitted light.

12. Apparatus for the examination of the female breast for tumors or the like, comprising
   a. a pair of spaced, generally parallel plates transparent to light, the plates having aligned edges gently concaved to fit snugly against the human chest wall in the vicinity of the breasts;
   b. means supporting the plates relative to each other and permitting at least one of the plates to move toward and away from the other plate to enable the breast to be captured and gently compressed and flattened between the plates;

c. light absorbing means positionable against exposed edges of the compressed, flattened breast received between the plates and capable of substantially preventing the escape of light from the breast edges;

d. a source of visible light positionable exteriorly of the plates for producing a beam of light directable through the plates and breast and generally normal to the plane of the plates, the light source including means permitting the diameter of the beam of light to be manually adjusted.

13. The apparatus of claim 12 wherein at least one of the plates includes visible indicia thereon defining a path for the beam of light to follow, the pathway being configured to cause illumination of substantially the entire breast section when the light beam is caused to follow the pathway from one end thereof to the other.

14. The apparatus of claim 12 including means permitting at least one of the plates to tilt upwardly about an axis generally parallel to the concavely curved edge of the plate.

15. A method for simply and harmlessly detecting tumors or the like in the female breast comprising compressing and flattening the breast between a pair of plates transparent to visible light, passing a beam of light from a movable light source in a direction normal to and through the plates and breast between the plates, moving the light source so as to illuminate substantially all portions of the breast tissue captured between the plates, and viewing the beam of light through the plates and breast tissue to detect areas of breast tissue having lesser transparency and which may be suggestive of tumor growth.

16. The method of claim 15 including the step of varying the diameter of the light beam as the beam is viewed through the plates and breast.

* * * * *